United States Patent [19]

Carr et al.

[11] 4,259,574
[45] Mar. 31, 1981

[54] MICROANALYSIS BY PULSE LASER EMISSION SPECTROSCOPY

[75] Inventors: Timothy W. Carr, Poughkeepsie; Howard A. Froot, Hopewell Junction, both of N.Y.

[73] Assignee: International Business Machines Corporation, Armonk, N.Y.

[21] Appl. No.: 91,855

[22] Filed: Nov. 6, 1979

[51] Int. Cl.³ .............................................. G09K 3/00
[52] U.S. Cl. ................................. 250/302; 250/461 R
[58] Field of Search ................ 250/302, 461 R, 461 B

[56] References Cited

U.S. PATENT DOCUMENTS

| | | | |
|---|---|---|---|
| 3,832,558 | 8/1974 | Fern | 250/461 |
| 4,006,360 | 2/1977 | Mueller | 250/461 B |
| 4,058,732 | 11/1977 | Wieder | 250/461 |
| 4,087,685 | 5/1978 | Froot | 250/302 |

*Primary Examiner*—Bruce C. Anderson
*Attorney, Agent, or Firm*—Henry Powers

[57] ABSTRACT

A system for detecting and identifying the composition of a material, such as semiconductor wafers and chips, subject to one or more stages of processing. The material is laser irradiated to induce molecular fluorescence with means to detect the decay rate of the fluorescence. The decay rate is then compared with a decay record of fluorescence of acceptable modifications of the material, inclusive of amalgamated contaminants or impurities (e.g. doped regions) to determine the state of the modification of the material.

18 Claims, 4 Drawing Figures

MICROANALYSIS BY PULSE LASER EMISSION SPECTROSCOPY

DESCRIPTION

1. Technical Field

This invention relates to the microanalysis of the composition of a material by pulsed laser emission spectroscopy, and more particular to the detection and/or identification of the chemical modification of semiconductor substrates, inclusive of amalgamated contaminants and/or impurities therein, by utilization of the decay rate of induced molecular fluorescence thereof.

One object of the present invention is to provide a novel system capable of rapidly and nondestructively monitoring and identifying the composition of a material, inclusive of silicon semiconductor substrates.

Another object of the present invention is to provide a novel system which allows either on-line or off-line identification of the modification of the composition of a material in processing thereof.

Another object of the present invention is to provide a novel system for identification of the composition of a material by use of the decay rate or lifetime of electromagnetic emission or molecular fluorescence from the materials' excited electronic state to a lower electronic state as a result of excitation by irradiation.

2. Background Art

Since the main thrust of the semiconductor industry is to manufacture devices with smaller and denser geometries the ability to monitor and identify compositional modifications of the basic semiconductor substrate in processing, becomes essential to the success of a manufacturing process. This includes designed modification of the material (e.g. doped regions) as well as composition alterations by amalgamation of deleterious contaminants.

The requirements for monitoring the compositional integrity of a semiconductor substrate are distinguishable from (even though supplemental to) systems for detection and identification of discrete organic contaminants carried on or embedded in a substrate, as for example, the system described in U.S. Pat. No. 4,087,685 issued on May 2, 1978 to H. A. Froot, a coinventor in this application. In this patent the system comprises means for and the steps of detecting and identifying organic luminescent material as small as submicron, which is carried on or embedded in a device, by exposing the substrate to electromagnetic radiation of sufficient energy to cause the organic material to luminesce, detecting the luminescent emission spectra of the organic materials, and comparing the spectra with known spectra of organic materials, used in the manufacturing process, to identify one or more of the luminescent materials. In practice, the emission spectra of the known materials are stored in a computer, and as the spectra of the unknown contaminants on the device are detected and generated, the generated spectra are compared with all of the stored spectra until a one-on-one match is obtained, thereby identifying the specific contaminant. Although this system provides a means of identifying discrete contaminant particulates, it does not provide information of the modification and/or alteration in the composition of a substrate, or device, as a result of process designed changes or by undesired amalgamation of contaminants.

BRIEF DESCRIPTION OF DRAWINGS

In the accompanying drawings forming a material part of this disclosure.

DISCLOSURE OF INVENTION

Figure 1:
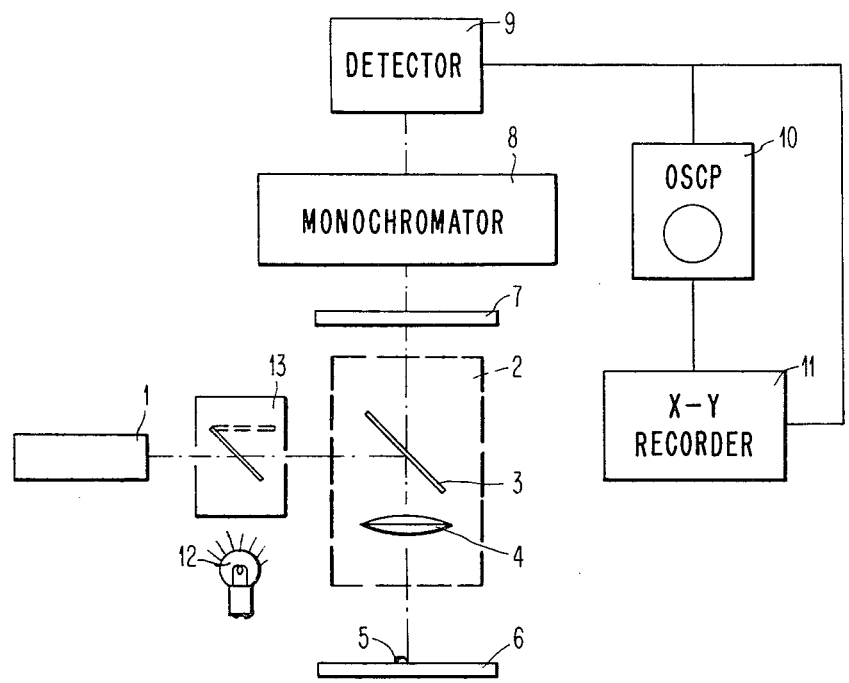
FIG. 1 is a schematic block diagram illustrating an embodiment of this invention.

This invention comprehends the irradiation of a material using UV-visible pulsed (e.g. $10^{-9}$ second pulse width) monochromatic laser light. Although the invention has general application to broad ranges of materials, it has special interest to the electronic field, inclusive of semiconductors, gas display panels, light emitting diodes, etc. For purposes of this description, the invention is directed to its use with silicon semiconductor substrates, processed for device fabrications, such as integrated circuits.

The substrate can be irradiated through the objective of an optical microscope so as to provide a small area resolution, as for example of the order of one micron. In this manner, the effects on the composition of a material after processing either by process design modification or by deleterious amalgamation of contaminants, upon the fluorescence and radiation lifetimes of the electronically excited states of the material can be examined. By choosing the proper wavelength of light, e.g. laser, selective excitation of various semiconductor device structures can be achieved. For example, with a semiconductor substrate having sequential composite coatings of silicon dioxide and silicon nitride, the silicon nitride composition can be selectively examined in the presence of the silicon dioxide layer. With a choice of an appropriate detector, both the optical emission and absorption spectra of a semiconductor structure and any absorbed or amalgated contamination, that may be present, can be examined and recorded. This technique does not require any special sample preparation, and is an in-situ, non-destructive analysis having a rapid turnaround time.

DISCUSSION

When silicon semiconductor structures or devices are irradiated with UV-visible light with energies of 2 to 6 electron volts (e.V.) the molecules of the semiconducture structure or device will be excited to higher level electronic states. Basically two types of electronic transition may be involved in the absorption of the UV-visible light. First, the electronic transition may involve the promotion of an electron from a localized orbital on one ion (or molecule) to a higher energy but still localized orbital, or second, the promoted electron may go to a collective energy level for the system called the conduction band. If as in the first case, the excited electron is localized on the same ion or molecule the new state is described as an "exciton" and the associated absorption band is called an exciton band. However, if the excitation transfers the electron to an orbital lying wholly or partly on another atomic species, then the observed absorption is generally called a charge transfer process or interionic transition.

Molecular fluorescence and phosphorescence occurs when an electron returns to a lower electronic state, with the emission of energy in the form of light. This process is referred to as a radiative transition. The probability that a molecule in an excited state will spontaneously undergo a radiative transition to a lower electronic state is given by $$A_{nm} = \frac{64 \pi^4 \omega_{mn}^2 e^2}{3h} g_m D_{nm}$$

$A_{nm}$ is the Einstein probability of spontaneous emission; the fraction of molecules in state n which undergo transistion per second to state m. Here $\omega_{nm}$ is the energy of the transition in wave number, $g_m$ is the degeneracy of state m, $D_{nm}$ is the dipole strength or the square of the transition-moment integral, and the other symbols have their usual meanings.

The transition-moment integral is defined by $$R_{mn} = \int \Psi_m M \Psi_n \, d\tau$$

where $\Psi_m$ and $\Psi_n$ are the total electronic wave functions of the initial and final state, M is the dipole moment vector and the integral is taken oven all space $d\tau$. It is the value of this integral which is largely responsible for the probability of emission. If the magnitude of this integral is equal to zero then the transition is said to be forbidden. If, however, the magnitude of the integral is not equal to zero then the corresponding transition is said to be allowed.

The radiative lifetime of an excited electronic state, ($\tau_o$) is the lifetime of the state if emission of radiation is the only mode of deactivation. The radiative lifetime is related to the Einstein coefficient for spontaneous emission by $\tau_o = 1/A_{nm}$ and has the units of seconds per transition. However, the emission of light is not the only means of giving up energy by the excited molecule and returning to a lower electronic energy level. There are several nonradiative processes by which the molecule can lose energy of which the most common are internal conversion and intersystem crossing on the same molecule and intermolecular energy transfer between molecules.

Internal conversion is a nonradiative transfer of electronic energy of an excited state to a high lying vibrational level of a lower electronic state of the same multiplicity. This process occurs when the potential-energy curve of the higher excited state crosses or comes near a high lying vibrational level of the lower electronic state. The lower electronic state will contain a large amount of vibrational energy but this will be lost rapidly by collisions with molecules and degraded to thermal energy.

Internal conversion to the ground electronic state will take place with a reduction in the fluorescence intensity. Internal conversion from higher excited states to lower excited states is more common, especially for polyatomic molecules which have potential energy surfaces with numerous intersections.

Intersystem crossing is the nonradiative energy transfer of an excited state to a lower electronic state of different multiplicity. This process occurs when the potential-energy curve of the higher state crosses that of the lower state provided the vibrational level is below that to which the molecule has been originally excited.

One of the most important processes by which an electronically excited state can lose energy is the nonradiative transfer from one molecule to another. The term intermolecular energy transfer refers to the one step non radiative energy transfer from a donor molecule $D^*$ to an acceptor molecule A. This type reaction is represented by $$D^* + A \rightarrow A^* + D$$

Several requirements are necessary for this reaction to become an important mode of deactivation. First, the energy level of the excited donor molecule must be higher than the energy level of the acceptor molecule to which it is transferring its energy. Secondly, the radiative lifetime of the excited donor must be longer than the time it takes for reaction to occur. If this were not the case then the excited donor would be deactivated by emission of radiation before the bimolecular quenching reaction could take place. A third requirement is that the overall spin angular momentum of the system should not change. This requirement is known as the Wigner spin conservation rule.

Theory provides us with two different mechanisms for the nonradiative transfer of electronic energy. One is the transfer of energy resulting from the collision of two molecules and the other is the transfer of energy between two molecules separated by distances greater than their collisional diameters.

Collisional or exchange energy transfer is a process in which the excited donor molecule, $D^*$, and the acceptor molecule, A, approach each other close enough for their electron clouds to overlap. The electrons in the overlap area are indistinguishable. An exchange mechanism occurs when the excited electron of the donor appears on the acceptor and an unexcited electron of the acceptor appears on the donor. The molecules then move apart with a resulting transfer of energy.

A second type of energy transfer mechanism is referred to as resonance-excitation transfer or long range energy transfer. In this process the excitation energy is transferred between two molecules separated by a distance considerably greater than the collisional diameter. The process is thought to result from a weak dipole-dipole interaction between the donor and acceptor molecules. A quantum mechanical relationship was derived by Forster Z. Electrochem. 64, 157, (1960) showing that the probability of energy transfer depends on the emission spectrum of the donor and the absorption spectrum of the acceptor. If the emission spectrum of the donor strongly overlaps the absorption spectrum of the acceptor then the probability of energy transfer will be high. Obviously the rate of energy transfer by this mechanism is dependent upon the separation of the two molecules. An expression for the relation of the rate constant for resonance-energy transfer to the distance separation.

$$\text{Rate constant } (D^* \rightarrow A^*) = 1/\tau_D (R_o/R)^6$$

where $\tau_D$ is the acutal means lifetime of the donor, R is the separation between $D^*$ and A, and Ro is the critical separation of donor and acceptor for which emission from $D^*$ equals the energy transfer from $D^*$ to A.

Once these other electronic states are populated through either a radiative or nonradiative process and if they are above the ground electronic state then they can emit light or undergo any of the above mentioned transitions. This gives rise to the typical emission band, which are a "fingerprint" of the material analyzed called the emission spectrum.

When an impurity is introduced or amalgamated into the semiconductor material there may or may not be a change in the emission spectrum of the device. This is because there are nonradiative transitions which are possible as described above. However, what will change, as an impurity (a conductivity determining dopant) or contaminant is introduced, is the lifetime of the excited state. The introduction of the impurity will give rise to other pathways for deactivation which will affect the lifetime of, in other words, the rate at which light is emitted from the excited electronic state.

The esseence of this invention is that the lifetime of the various electronic states can be measured directly with spatial resolution of the semiconduction material on the order of one micron. The manner in which this measurement is made and a description of the instrument is presented below.

BEST MODE FOR CARRYING OUT THE INVENTION

In FIG. 1, the system of the invention is illustrated and includes an excitation source 1 capable of generating picosecond pulses at various wavelengths. The Spectra-Physics System utilizing their Model 375 Dye Laser and Model 171 Ion Laser, is one example of an appropriate source.

The source is employed with a normal incidence optical microscope, such as a Leitz Orthoplan, for deflecting and focussing the excitation source onto the specimen 5. This is accomplished by using a standard beam deflector 3 and appropriate objectives 4. The area of interest on the sample is brought into the excitation beam by means of a conventional microscope mechanical stage 6.

The light emitted by the sample passes through an appropriate narrow band filter 7, (which blocks reflected portions of the basic excitation beam) and then followed by passing through a monochromator 8 (such as the SPEX Model 1500) which scans the emitted light.

A detector 9, such as on RCA 8575 photomultiplier (PMT), detects the emitted light. The signal from the PMT 9 can be suitably stored as in a Tektronix 564B sample storage oscilloscope 10, and recorded by suitable means 11 such as a H-P7035B X-Y recorder.

Visual examination of the sample is accomplished by switching to a normal light source 12 by means of a pivoting mirror assembly 13.

EMISSION SPECTRA

Figure 2:
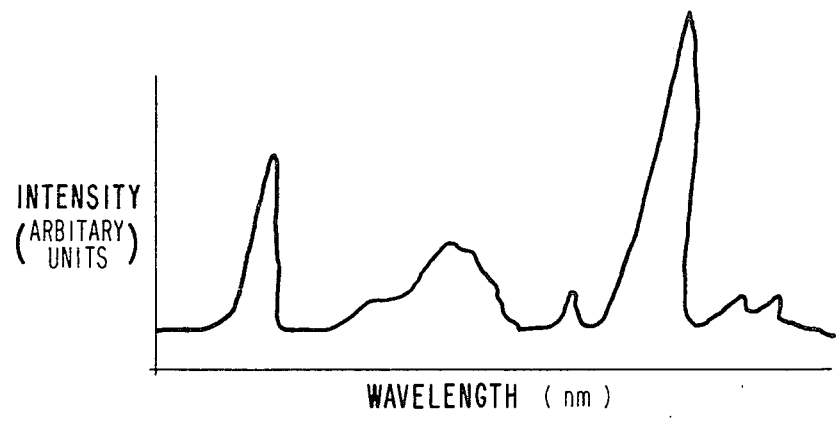
FIG. 2 is a graph illustrating a typical plot of intensity versus wavelength, as obtained in accordance with this invention.

To obtain the optical emission spectra from a sample, the sample is placed on the mechanical stage of the microscope and by choosing the proper objective lens of the microscope which is dependent upon the size of the area to be examined and then the sample is brought into focus. After visual examination of the sample the light source is switched to the laser source by means of the pivoting mirror assembly 13 in FIG. 1. The laser may be operated in either the continuous or pulsing mode. The monochromator scans the wavelength's range from the wavelength of the laser light upto the infrared region of the spectra. The output of the photomultiplier detector is recorded on a strip chart recorder or X-Y plotter. The plot generated will be intensity as a function of wavelength (as illustrated in FIG. 2).

LIFETIME MEASUREMENTS

Figure 3:
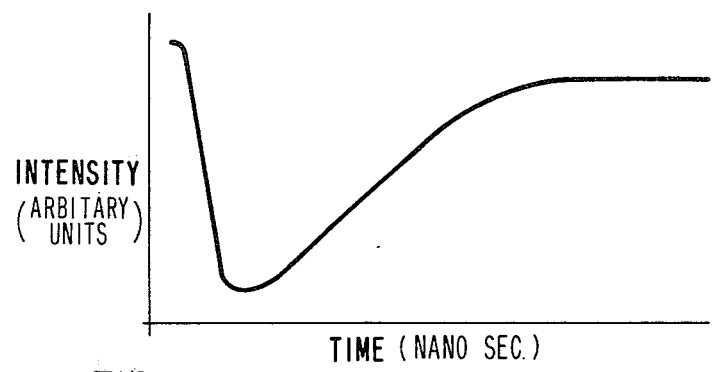
FIG. 3 is a graph illustrating a plot generated in accordance with the invention showing intensity as a function of time.
Figure 4:
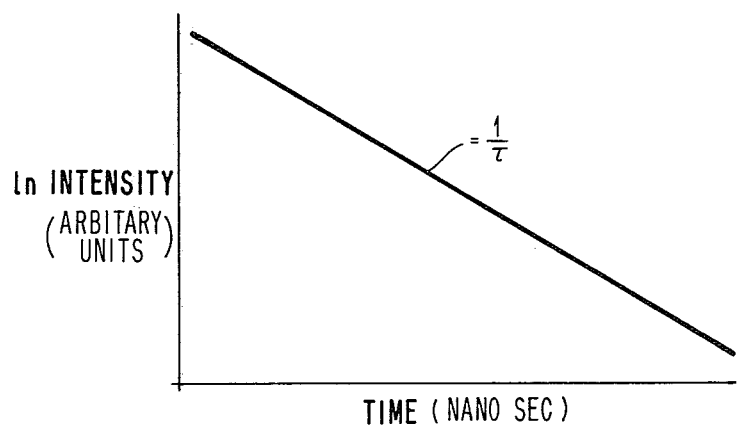
FIG. 4 is a graph illustrating the decay portion of FIG. 3 as the logorithm of the decay intensity as a function of time.

To determine the lifetimes of the electronically excited states the laser must be operated in the pulsing mode and the monochromator must be set at a specific wavelength. The wavelength of interest is selected from the emission spectra. The fast rise time photomultiplier is connected to a fast risetime sampling-storate oscilloscope (such as the Tektronix 564B) which is connected to an X-Y recorder. The plot which is generated is the detected light intensity of the specific wavelength as a function of time as illustrated in FIG. 3. To calculate the lifetime of the excited state the fluorescence decay portion of FIG. 3 is plotted as the logorithm of the decay intensity as a function of time as illustrated in FIG. 4. The slope of the line generated in FIG. 4 is the rate constant for transition which is the reciprocal of the lifetime. The lifetime is represented as $\tau$ in FIG. 4.

In another form of the invention, and in the manner discussed in the aforesaid patent U.S. Pat. No. 4,087,685, fluorescent decay rates of the acceptable compositions of the semiconductor substrate at the end of each or selected stages of processing can be stored in a computer, and as data of each real-time analysis is obtained it is compared with the stored data for a one-on-one match which enables analysis of the substrate's composition. As indicated above, the compositional modifications of the various substrate elements can comprise designed process modifications (e.g. forming doped regions, dielectric isolation, coatings and the like) and, compositional alterations due to absorbed and/or amalgated impurities (e.g. from resist coating, etching operations and the like). The stored data can comprise tolerance acceptable limits for process designed composition modifications as well as allowable tolerances or limits of undesired contamination levels absorbed and/or amalgamated in the substrate. Also, as previously indicated the measurements and analyses can be performed either on-line or off-line.

While the invention has been illustrated and described with respect to preferred embodiments thereof, it is to be understood that invention is not to be limited to the precise constructions and embodiments herein disclosed, and the right is reserved to all changes and modifications coming within the scope of the invention as defined in the appended claims.

Having thus described the invention, what is claimed as new, and desired to be secured by Letters Patent is:

1. System for identifying the composition of a material subjected to at least one stage of processing in a manufacturing line, comprising:

means for providing a record of known decay rates of the molecular fluorescence, from the excited to a lower energy state, of said material of acceptable modification thereof at the end of each stage of processing, means at the end of each state of processing for laser irradiating said material to induce molecular fluorescence thereof, means for detecting the decay rate of said induced fluorescence, and means for comparing said detected decay rate with said record to determine the state of modification of each material.

2. The system of claim 1 wherein said irradiation is at a pulsed rate.

3. The system of claim 1 wherein said irradiation is pulsed at a $10^{-9}$ second pulse width.

4. The system of claim 1 wherein said irradiation is with ultraviolet-visible light with energies ranging from about 6 ev. to about 2 ev.

5. The system of claim 4 wherein said irradiation is at a pulsed rate.

6. The system of claim 4 wherein said irradiation is pulsed at a $10^{-9}$ second pulse width.

7. The system of claim 1 wherein said system is off-line of said manufacturing line.

8. The system of claim 1 wherein said material is a silicon semiconductor substrate.

9. The system of claim 7 wherein said material is a silicon semiconductor substrate.

10. A system for identifying the composition of a material subjected through various stages of processing in a manufacturing line, comprising:

means for providing a record of known decay rates of the molecular fluorescence from the excited to lower energy states of said material, by irradiation thereof, of anticipated chemical modifications inclusive of amalgamated contaminations thereof through said processing stages, means associated with said processing stages for laser irradiation of said material to induce molecular fluorescence thereof, means for detecting the decay rate of said induced fluorescence, and means for comparing said detected decay rate with said record to determine the state of modification of said material.

11. The system of claim 10 wherein said irradiation is at a pulsed rate.

12. The system of claim 10 wherein said irradiation is pulsed at a $10^{-9}$ second pulse width.

13. The system of claim 10 wherein said irradiation is with ultraviolet-visible light with energies ranging from about 6 ev. to about 2 ev.

14. The system of claim 13 wherein said irradiation is at a pulsed rate.

15. The system of claim 13 wherein said irradiation is pulsed at a $10^{-9}$ second pulse width.

16. The system of claim 10 wherein said material is a silicon semiconductor substrate.

17. The system of claim 10 wherein said system is off-line of said manufacturing line.

18. The system of claim 17 wherein said material is a silicon semiconductor substrate.

* * * * *